United States Patent [19]

Lernhardt

[11] Patent Number: 5,331,090

[45] Date of Patent: Jul. 19, 1994

[54] CR2 LIGAND COMPOSITIONS AND METHODS FOR MODULATING IMMUNE CELL FUNCTIONS

[75] Inventor: Waldemar Lernhardt, Solana Beach, Calif.

[73] Assignee: California Institute of Biological Research, La Jolla, Calif.

[21] Appl. No.: 404,679

[22] Filed: Sep. 8, 1989

[51] Int. Cl.⁵ .................... A61K 37/00; A61K 37/02; C07K 5/00; C07K 7/00
[52] U.S. Cl. .................................. 530/329; 530/328; 530/327
[58] Field of Search ............... 530/329, 328, 327, 330; 514/15, 16, 17, 18, 19

[56] References Cited

PUBLICATIONS

Sernis et al., J. of Immunology, vol. 142 No. 7, pp. 2207–2212, Apr. 1989.
Tsokos et al., J. of Immunology, vol. 144, No. 5, pp. 1640–1645, Mar. 1990.
Carter et al., J. of Immunology, vol. 143, No.6, pp. 1755–1760, Sep. 1989.
Gisler et al., Molecular Immunology, vol. 25, No. 11 pp. 1113–1127, 1988.
Franke et al., Proc. Natl. Acad. Sci. USA, 86:4027–4031 (1989).
Nemerow et al., Cell, 56:369–377 (1989).
Lambris et al., Proc. Natl. Acad. Sci. USA, 82:4235–4239 (1985).
Lernhardt et al., Immunol. Rev., 99:241–262 (1987).
Melchers et al., Proc. Natl. Acad. Sci. USA, 82:7681–7685 (1985).
Tanner et al., J. Virol., 62:4452–4464 (1988).

*Primary Examiner*—Lester L. Lee
*Assistant Examiner*—A. M. Davenport
*Attorney, Agent, or Firm*—Thomas Fitting

[57] ABSTRACT

Synthetic polypeptides corresponding to the B lymphocyte CR2 receptor binding site present on a CR2 ligand are disclosed together with polypeptide aggregates, compositions, anti-polypeptide antibodies and methods of preparing and using the polypeptides and antibodies.

2 Claims, 11 Drawing Sheets

FIG.1A

```
  1 GAATTCCCACCTGGCGTGCCCTCCGTCAGCAGCAAGGGCATCATGGAG                              2
                                                  M  E
 48 GAGGATGAGGCCTGCGGGCGCCAGTACACGCTCAAGAAAACCACCACT                             18
     E  D  E  A  C  G  R  Q  Y  T  L  K  K  T  T  T
 96 TACACCCAGGGGGTGCCCCCCAGCCAAGGTGACCTGGAGTACCAGATG                             34
     Y  T  Q  G  V  P  P  S  Q  G  D  L  E  Y  Q  M
144 TCCACACAACAGCCAGGGCCAAACGGGTGCGGGAGGCCATGTGCCCTGGT                            50
     S  T  T  A  R  A  K  R  V  R  E  A  M  C  P  G
192 GTGTCAGGCGAGGACAGCTCGCTTCTGCTGGCCACCCAGGTGGAGGGG                             66
     V  S  G  E  D  S  S  L  L  L  A  T  Q  V  E  G
```

FIG.1B

```
240  CAGGCCACCAACCTGCAGGCGACTGGCCGAGCCGTCCCAGCTGCTCAAG      82
      Q  A  T  N  L  Q  R  L  A  E  P  S  Q  L  L  K

288  TCGGCCATTGTGCATCTCATCAACTACCAGGACGATGCCGAGCTGGCC      98
      S  A  I  V  H  L  I  N  Y  Q  D  D  A  E  L  A

336  ACTCGCGCCCTGCCCGAGCTCACCAAACTGCTCAACGACGAGGACCCG     114
      T  R  A  L  P  E  L  T  K  L  L  N  D  E  D  P

384  GTGGTGGTGACCAAGGCGGCCATGATTGTGAACCAGCTGTCGAAGAAG     130
      V  V  V  T  K  A  A  M  I  V  N  Q  L  S  K  K

432  GAGGCGTCGCGGCGCGCCCTGATGGCCTCCCCAGCTGGTGGCCGCTGT     146
      E  A  S  R  R  A  L  M  A  S  P  A  G  G  R  C
```

FIG.1C

```
480  CGTGGCGTACCATGCAGAATACCAGCGACCTGGACACAGCCCGCTGCAC    162
      R   A   Y   H   A   E   Y   Q   R   P   G   H   S   P   L   H

528  CACCAGCATCCTGCACAACCTCTCCCACCGGGAGGGGCTGCTCGC      178
      H   Q   H   P   A   Q   P   L   P   P   P   G   G   A   A   R

576  CATCTTCAAGTCGGGGTGGCATCCCCTGCTCTGGTCCGCATGCTCAGCTC   194
      H   L   Q   V   G   W   H   P   C   S   G   P   H   A   Q   L

624  CCCTGTGGAGTCGGTCCTGTTCTATGCCATCACCACGCTGCACAACCT    210
      P   C   G   V   G   P   V   L   C   H   H   H   A   A   Q   P

672  GCTCCTGTACCAGGAGGGCCAAGATGGGCCGTGCCCTGGCCGACGG      226
      A   P   V   P   G   G   R   Q   D   G   R   A   P   G   R   R
```

FIG.1D

```
720  GCTGCAAAAGATGGTGCCCCTGCTCAACAAGAACAACCCCAAGTTCCT  242
      A  A  K  D  G  A  P  A  Q  Q  E  Q  P  Q  V  P

768  GGCCATCACCACCGACTGCCTGCAGCTCCTGGCCTACGGCAACCAGGA  258
      G  H  H  H  R  L  P  A  A  P  G  L  R  Q  P  G

816  GAGCAAGCTGATCATCCTGGCCAATGGTGGGCCCCAGGCCTCGTGCAG  274
      E  Q  A  D  H  P  G  Q  W  A  P  G  L  V  Q

864  ATCATGCGTAACTACAGTTATGAAAAGCTGCTCTGGACCACCAGTCGT  290
      I  M  R  N  Y  S  Y  E  K  L  L  W  T  T  S  R

912  GTGCTCAAGGTGCTATCCGTGTGTCCCAGCAATAAGCCTGCCATTGTG  306
      V  L  K  V  L  S  V  C  P  S  N  K  P  A  I  V
```

FIG.1E

```
960  GAGGCTGGTGGGATGCAGGCCCTGGGCAAGCACCTGACCAGCAACAGC
      E  A  G  G  M  Q  A  L  G  K  H  L  T  S  N  S   322

1008 CCCCGCCTGGTGCAGAACTGCCTGTGGACCCTGCGCAACCTCTCAGAT
      P  R  L  V  Q  N  C  L  W  T  L  R  N  L  S  D   338

1056 GTGGCCACCAAGCAGGAGGGCCTGGAGAGTGTGCTGAAGATTCTGGTG
      V  A  T  K  Q  E  G  L  E  S  V  L  K  I  L  V   354

1104 AATCAGCTGAGTGTGGATGACGTCAACGTCCTCACCTGTGCCACGGGC
      N  Q  L  S  V  D  D  V  N  V  L  T  C  A  T  G   370

1152 ACACTCTCCAACCTGACATGCAACAACAGCAAGAACAAGACGCTGGTG
      T  L  S  N  L  T  C  N  N  S  K  N  K  T  L  V   386
```

FIG. 1F

```
1200 ACACAGAACAGGGTGTGGAGGCTCTCATCCATGCCATCCTGCGTGCT
      T  Q  N  S  G  V  E  A  L  I  H  A  I  L  R  A    402

1248 GGTGACAAGGACGACATCACGGAGCCTGCCGTCTGCGCTCTGCGCCAC
      G  D  K  D  D  I  T  E  P  A  V  C  A  L  R  H    418

1296 CTCACTAGCCGCCACCCTGAGGCCGAGATGGCCCAGAACTCTGTGCGT
      L  T  S  R  H  P  E  A  E  M  A  Q  N  S  V  R    434

1344 CTCAACTATGGCATCCCAGCCATCGTGAAGCTGCTCAACCAGCCCAAC
      L  N  Y  G  I  P  A  I  V  K  L  L  N  Q  P  N    450

1392 CAGTGGCCACTGGTCAAGGCAACCATCGGCTTGATCAGGAATCTGGCC
      Q  W  P  L  V  K  A  T  I  G  L  I  R  N  L  A    466
```

FIG. 1G

```
1440 CTGTGCCCAGCCAACCATGCCCCGCTGCAGGAGGCAGGCGGTCATCCCC
      L  C  P  A  N  H  A  P  L  Q  E  A  A  V  I  P   482

1488 CGCCTCGTCCAACTGCTGGTGAAGGCCCACCAGGATGCCCAGCGCCAC
      R  L  V  Q  L  L  V  K  A  H  Q  D  A  Q  R  H   498

1536 GTAGCTGCAGGCACACAGCAGCCCTACACGGATGGTGTGAGGATGGAG
      V  A  A  G  T  Q  Q  P  Y  T  D  G  V  R  M  E   514

1584 GAGATTGTGGAGGGCTGCACCGGAGCACTGCACATCCTCGCCCGGGAC
      E  I  V  E  G  C  T  G  A  L  H  I  L  A  R  D   530

1632 CCCATGAACCGCATGGAGATCTTCCGGCTCAACACCATTCCCCTGTTT
      P  M  N  R  M  E  I  F  R  L  N  T  I  P  L  F   546
```

FIG.1H

```
1680  GTGCAGCTCCTCTGTACTCGTCGGTGGAGAACATCCAGCGCGTGGCTGCC        562
        V  Q  L  L  Y  S  S  V  E  N  I  Q  R  V  A  A

1728  GGGGTGCTGTGTGAGCTGGCCCAGGACAAGGAGGCGGCCACGCCCATTG        578
        G  V  L  C  E  L  A  Q  D  K  E  A  A  T  P  L

1776  ATGCAGAGGGCCTCGGCCCCACTCATGGAGTTGCTGCACTCCCGCAAC        594
        M  Q  R  A  S  A  P  L  M  E  L  L  H  S  R  N

1824  GAGGGCACTGCCACCTACGCTGCCGCTGTTCCGCATCTCCGAG          610
        E  G  T  A  T  Y  A  A  A  V  L  F  R  I  S  E

1872  GACAAGAACCCAGACTACCGGAAGCGCGTGTCCGTGAGCTCACCAAC        626
        D  K  N  P  D  Y  R  K  R  V  S  V  E  L  T  N
```

FIG. 1I

```
1920 TCCCTCTTCAAGCATGACCCGGCTGCCTGGAGGCTGCCCAGAGCATG  642
      S  L  F  K  H  D  P  A  A  W  E  A  A  Q  S  M

1968 ATTCCCATCAATGAGCCCTATGGAGATGACTTGGATGCCACCTACCGC  658
      I  P  I  N  E  P  Y  G  D  D  L  D  A  T  Y  R

2016 CCCATGTACTCCAGCGATGTGCCCCTTGACCCGCTGGAGATGCACATG  674
      P  M  Y  S  S  D  V  P  L  D  P  L  E  M  H  M

2064 GACATGGATGGAGACTACCCCATCGACACCTACAGCGACGCTCAGGCC  690
      D  M  D  G  D  Y  P  I  D  T  Y  S  D  A  Q  A

2112 CCCGTACCCCACTGCAGACCACATGCTGCCTAGGCGGCCTGGCCCCA   700
      P  V  P  H  C  R  P  H  A  A
```

FIG.1J

```
2160  TGCGGTTCCTCATCTGAGAGGCTCTCCGTGCAGGCGATGGGCAAGAC
2208  AAGAAAGTGCCTGAGCTGGGGAAGCAGGGGGTGTAACTTCCTGCTGCA
2256  CCCTGCGCCTCCAGAGGTCCTCCGTAGGGTCTTTCTTGGGATAGTGTT
2304  CTGCTCCTGCTTTTCTGTCCTGGGCATGGGTCCAGGGCCTGACACCCC
2352  CTCCCCGCCCTTGGCCCTGGCCACTAAAGCTTCAGACTCAAGTACCC
2400  ATTCTGTTTCCCCCAGCAACGCCCCTCCAAACCTCCAGCCTCCCTGT
2448  CTCCAGCTGCCTGGGCCCGGAAGGGCTTTGGTTCCTTCTCTGGGTCTG
2496  ATTTTCTCACTGAACTCCACCGACCAACTGCCCTAAGCCCCCCAGGCCT
2544  CCAGGGCCCAGGTTCGAGACCCAAACCCCCAAAATCCAAAACTTCTCT
```

FIG. 1K

```
2592  TGAAAAGTTCAGGGACCGTCCAGGGGAGATGGGGAGGAGATATGGAGT
2640  GAGTCACCTGCTCCAGAAGATGCCAGCTTCTCTCTCCAGGTGCTTAG
2688  TTGGCTTTGCCACCCCTCACTCCCCAGGGAGCTCTGGGACAGCTTCC
2736  TCACACCCCTGTCCCACCCACACAGCTGCCCTAGCTGACCCCGAGAAG
2784  TGCTCTTGGCTGACCCCCTCTGGTGTGGTGAGGGGCTTTCTCTTCCC
2832  CTTCCTGTTTCAGACCCCCCCATTTCCCGCACATGGTGTGGGGGCTC
2880  GGGGAGGTCCAAGCAGAGTGTTTATTATTATCGCTTTATGTTTTTGG
2928  TTATTGGTTTTTTTGTATAGACCAAAGCAAAGAAAATAAAAATGGAAT
2976  TC
```

CR2 LIGAND COMPOSITIONS AND METHODS FOR MODULATING IMMUNE CELL FUNCTIONS

This invention was made with government support under government contract 5 RO1 CA43119 awarded by the National Institutes of Health. The government has certain rights in the invention.

TECHNICAL FIELD

The present invention relates to the CR2 binding region of a CR2 ligand and to polypeptides and polypeptide aggregates that contain the binding region. More particularly, the present invention contemplates CR2 ligand-containing compositions, antibodies to CR2 ligands, rDNA's that express CR2 ligands and methods of using the ligands and the anti-ligand antibodies.

BACKGROUND OF THE INVENTION

CR2 (CD21) is a cellular receptor on B lymphocytes that is implicated in their growth regulations and is linked to intercellular pathways involved in signalling B cell proliferation. Melchers et al., Nature, 317:264 (1985); Lernhardt et al., Immunol. Rev., 99:239 (1987); Bohnsack et al., J. Immunol., 141:2569 (1988); Cooper et al., Ann. Rev. Immunol., 6:85 (1988); Tedder et al., J. Clin. Immunol., 6:65 (1986); Hatzfeld et al., J. Immunol., 140:170 (1988); Frade et al., Proc. Natl. Acad. Sci. USA, 82:1490 (1985).

CR2 occurs on normal B lymphocytes and on B cell neoplasms. Cooper et al., Ann. Rev. Immunol., 6:85 (1988); Hatzfeld et al., J- Immunol., 140:170 (1988). CR2 functions as a receptor for several complement C3 activation products. The proteolytic C3 activation products iC3b, C3dg and C3d all bind to CR2 and have been shown to mediate both stimulating and inhibiting effects on lymphocytes. Weigle et al., in *Complement*, Muller-Eberhard, H.J. and Miescher, P.A. (eds.), p. 323, Springer-Verlag, Berlin (1985). Because of its central role in B cell function, CR2 function and ligands that modulate that function are of great interest.

The CR2 receptor is also of clinical interest because it is the receptor for the human herpes virus, Epstein-Barr virus. Fingeroth et al., Proc. Natl. Acad. Sci. USA, 86:242 (1989). EBV is the causative agent of infectious mononucleosis, [Henle et al., Proc. Natl. Acad. Sci. USA, 59:94 (1968)] and is possibly a human cancer virus, because it has been linked to nasopharyngeal carcinoma and Burkitt's lymphoma. Henle et al., Science, 157:1064 (1967). In addition, EBV is thought to be associated with x-linked lymphoproliferative disease (Duncan's disease) [Purtillo et al., Lancet i, 935, (1975)] and several human autoimmune disorders. Tosato et al., Adv. Immunol., 37:99 (1985). Lastly, EBV may play a role in the onset of B cell neoplasia observed in a substantial number of patients with AIDS (Yarchoan et al., J. Clin. Invest., 78:439 (1986). In vitro infectious EBV is a T cell-independent B cell stimulator and transforms human B lymphocytes to immortal polyclonal lymphoblastoid cell lines. Cooper et al., Ann. Rev. Immunol., 6:85 (1988). Non-transforming virus is a T cell-dependent B cell activator. Cooper et al., Ann. Rev. Immunol., 6:85 (1988). Drug inhibitors of EBV propagation that operate by interfering with virus binding to CR2 will therefore be of clinical relevance.

Some ligands that bind CR2 have been extensively characterized. For example, the exact sequence motif mediating binding of C3 fragments to CR2 has been elucidated by Lambris et al., Proc. Natl. Acad. Sci. USA, 82:4235 (1985) and has the amino acid composition LYNVEA. Peptides containing this motif have the ability to inhibit aggregated C3d-induced S phase entry of B cells [(Lernhardt, et al., Immunol. Rev., 99:239 (1987)] and to inhibit alpha B cell growth factor activity. Melchers, et al., Proc. Natl. Acad. Sci. USA, 82:7681 (1985). However, the precise function of a ligand containing this motif is unclear. Monomeric C3B and C3d are inhibitory, whereas aggregated C3b and C3d stimulate B cell proliferation. Erdei, et al., Eur. J. Immunol., 15:184 (1985); Bohnsack et al., J. Immunol., 141:2569 (1988).

BRIEF SUMMARY OF THE INVENTION

It has now been discovered that a new family of CR2 ligands exist that have the capacity to bind CR2 and modulate numerous CR2-mediated events occurring in normal and neoplastic B lymphocytes. This discovery arose when a new CR2 ligand-encoding gene was cloned and sequenced, and polypeptides corresponding to the CR2 binding site present on the CR2 ligand protein were determined.

Therefore, the present invention describes DNA segments that encode a CR2 ligand and CR2 ligand polypeptides that contain the binding site. Recombinant DNA (rDNA) molecules are also described that contain DNA segments that encode CR2 ligands, as well as rDNA expression vectors capable of expressing CR2 ligands in compatible hosts.

A CR2 ligand comprising a polypeptide is described having as a part of its amino acid residue sequence one or more CR2 binding sites represented by the formula: PAIVEAG or NSGVEA. In one embodiment a polypeptide aggregate is described having a plurality of polypeptides, each containing one CR2 binding site.

Also described are the therapeutic compositions containing CR2 ligands and methods of using those compositions to stimulate or inhibit B lymphocyte proliferation. In particular, inhibitory CR2 ligands containing only one CR2 binding site are described that are useful to inhibit B lymphocyte proliferation, such as in patients with B cell lymphoma. Further, stimulatory CR2 ligands are described that are useful to stimulate B lymphocytes and myelomas, such as in patients with immunodeficiencies or to boost production of immunoglobin secretion by hybridoma cultures.

A method of inhibiting infection in vitro or in vivo by Epstein Barr virus (EBV) is also described in which CR2 ligands are administered to bind CR2 receptor and thereby competitively block EBV infection of host cells by blocking virus binding to the cell receptor, CR2.

Antibody and monoclonal antibody compositions are contemplated that contain antibody molecules that immunoreact with a CR2 ligand of this invention, and more particularly immunoreact a CR2 ligand binding site for CR2.

Diagnostic systems and methods are also described for detecting the presence of CR2 ligand or anti-CR2 ligand antibodies in bodily fluid samples. The described systems and methods utilize the anti-CR2 ligand antibody compositions and CR2 ligands of the present invention.

BRIEF DESCRIPTION OF THE DRAWINGS

In the drawings, forming a portion of this disclosure:
FIGS. 1A–1K illustrates the nucleotide sequence of a cDNA that codes for a CR2 ligand of this invention, shown from left to right and in the direction of 5' terminus to 3' terminus using the single letter nucleotide base code. The structural gene for the mature CR2 ligand begins at base 42 and ends at base 2141, with the numbers for base residue positions indicated above the sequence.

The amino acid residue sequence for a CR2 ligand is indicated by the single letter code below the nucleotide base sequence, with the numbers for each residue position indicated below the amino acid residue sequence. The reading frame is indicated by placement of the deduced amino acid residue sequence above the nucleotide sequence such that the single letter that represents each amino acid is located above the middle base in the corresponding codon.

DETAILED DESCRIPTION OF THE INVENTION

A. Definitions

Amino Acid Residue: The amino acid residues described herein are preferred to be in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, J. Biol. Chem., 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues or to a amino-terminal $NH_2$ group or to a carboxy-terminal COOH group.

Polypeptide: refers to a linear series of amino acid residues connected to one another by peptide bonds between the alpha-amino group and carboxy group of contiguous amino acid residues.

Peptide: as used herein refers to a linear series of no more than about 50 amino acid residues connected one to the other as in a polypeptide.

Protein: refers to a linear series of greater than 50 amino acid residues connected one to the other as in a polypeptide.

Synthetic peptide: refers to a chemically produced chain of amino acid residues linked together by peptide bonds that is free of naturally occurring proteins and fragments thereof.

Antibody: The term antibody in its various grammatical forms refers to a composition containing immunoglobulin molecules and/or immunologically active portions of immunoglobulin molecules, i.e., molecules that contain an antibody combining site or paratope.

Antibody Combining Site: An "antibody combining site" is that structural portion of an antibody molecule comprised of heavy and light chain variable and hypervariable regions that specifically binds antigen.

Antibody Molecule: The phase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v).

Fab and F(ab')$_2$ portions of antibody molecules are prepared by the proteolytic reaction of papain and pepsin, respectively, on substantially intact antibody molecules by methods that are well known. See for example, U.S. Pat. No. 4,342,566 to Theofilopolous and Dixon. Fab' antibody molecule portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred, and is utilized as illustrative herein.

Probe Binding conditions: Probe Binding conditions are those that maintain the binding activity of the probes of this invention and C3 gene expression product sought to be assayed. Probe binding conditions vary, as is well known in the art, on the type of probe being used, e.g., antibody molecule or nucleic acid, and the gene expression product sought to be assayed e.g., polypeptide or in RNA.

Immunoreaction Conditions: Immunoreaction conditions are those that maintain the immunological activity of the anti-C3 antibody molecules used in this invention and the C3 polypeptide sought to be assayed. Those conditions include a temperature range of about 4 degrees C. to about 45 degrees C., preferably about 37 degrees C.; a pH value range of about 5 to about 9, preferably about 7 and an ionic strength varying from that of distilled water to that of about one molar sodium chloride, preferably about that of physiological saline. Methods for optimizing such conditions are well known in the art.

Monoclonal Antibody: The phrase "monoclonal antibody" in its various grammatical forms refers to an antibody containing having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and is represented herein by a formula whose left to right orientation is in the conventional direction of 5'-terminus to 3'-terminus.

Polynucleotide: A nucleic acid molecule comprising a polymeric unit of DNA or RNA having a sequence of two or more operatively linked nucleotides that form a single linear strand of nucleotides, also referred to as an oligonucleotide.

Duplex: A double-stranded nucleic acid molecule consisting of two strands of complementary polynucleotide hybridized together by the formation of a hydrogen bond between each of the complementary nucleotides present in a base pair of the duplex. Because the nucleotides that form a base pair can be either a ribonucleotide base or a deoxyribonucleotide base, the term "duplex" referring to either a DNA-DNA duplex comprising two DNA strands, or a RNA-DNA duplex comprising one DNA and one RNA strand.

Base Pair (bp): A partnership of adenine (A) with thymine (T), or of cytosine (C) with guanine (G) in a double stranded DNA duplex.

Nucleic Acid: A term to refer to any of a class of molecules that includes ribonucleic acid (RNA), deoxynucleic acid (DNA) in its single or double stranded forms, and polynucleotides.

Isolated polynucleotide: A term used to refer to a polynucleotide that is substantially free of contaminating proteins.

DNA segment: A DNA-DNA duplex having a preselected conserved nucleotide sequence and a sequence coding for a CR2 ligand of the present invention.

B. DNA Segments

In living organisms, the amino acid residue sequence of a protein or polypeptide is directly related via the genetic code to the deoxyribonucleic acid (DNA) sequence of the structural gene that codes for the protein and the mRNA from which it is translated. Thus, a nucleotide sequence can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences can code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

An isolated DNA segment of the present invention contains a nucleotide sequence that encodes a CR2 ligand polypeptide sequence of this invention. Typically, the CR2 ligand-encoding DNA segment is no more than about 5,000, and preferably no more than about 2,500, nucleotides in length. Representative nucleotide sequences that encode a CR2 ligand polypeptide of the present invention can include nucleotide sequences that correspond to the nucleotide base sequence shown in FIGS. 1A–1K. A preferred CR2 ligand polypeptide-encoding nucleotide sequence includes a nucleotide sequence that encodes the amino acid residue sequence shown in FIGS. 1D–1F from residue 389 to residue 394, or from residue 303 to residue 309. In a related embodiment, a preferred DNA segment includes a nucleotide sequence that encodes the amino acid residue sequence from residue 1 to residue 700 shown in FIGS. 1A–1I.

A DNA segment of the present invention that encodes a CR2 ligand polypeptide can easily be synthesized by chemical techniques, for example, the phosphotriester method of Matteucci, et al, *J. Am. Chem. Soc.*, 103:3185 (1981). Of course, by chemically synthesizing the coding sequence, any desired modifications can be made simply by substituting the appropriate bases for those encoding the native amino acid residue sequence.

C. Recombinant DNA Molecules

The present invention further contemplates a recombinant DNA (rDNA) that includes a DNA segment of the present invention operatively linked to a vector. A preferred rDNA is characterized as being capable of directly expressing, in a compatible host, a CR2 ligand. By "directly expressing" is meant that the mature polypeptide chain of the expressed CR2 ligand is formed by translation alone as opposed to proteolytic cleavage of two or more terminal amino acid residues from a larger translated precursor protein. Preferred rDNA's of the present invention are the rDNA plasmids pBS 9-4, pCMV 9-4 and pMSG 9-4 described in Example 5.

A rDNA molecule of the present invention can be produced by operatively linking a vector to a DNA segment of the present invention.

As used herein, the term "vector" refers to a nucleic acid molecule capable of transporting between different genetic environments another nucleic acid to which it has been operatively linked. Preferred vectors are those capable of autonomous replication and/or expression of nucleic acids to which they are linked. Vectors capable of directing the expression of genes to which they are operatively linked are referred to herein as "expression vectors". As used herein, the term "operatively linked", in reference to DNA segments, describes that the nucleotide sequence is joined to the vector so that the sequence is under the transcriptional and translation control of the expression vector and can be expressed in a suitable host cell.

The choice of vector to which a CR2 ligand-coding DNA segment is operatively linked depends directly, as is well known in the art, on the functional properties desired, e.g., replication or protein expression, and the host cell to be transformed, these being limitations inherent in the art of constructing recombinant DNA molecules.

In preferred embodiments, the vector utilized includes a procaryotic replicon i.e., a DNA sequence having the ability to direct autonomous replication and maintenance of the recombinant DNA molecule extra chromosomally in a procaryotic host cell, such as a bacterial host cell, transformed therewith. Such replicons are well known in the art. In addition, those embodiments that include a procaryotic replicon also include a gene whose expression confers a selective advantage, such as drug resistance, to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the CR2 ligand-coding segments in a bacterial host cell, such as E. coli transformed therewith. A promoter is an expression control element formed by a DNA sequence that permits binding of RNA polymerase and transcription to occur. Promoter sequences compatible with bacterial hosts are typically provided in plasmid vectors containing convenience restriction sites for insertion of a DNA segment of the present invention. Typical of such vector plasmids are pUCS, pUC9, pBR322, and pBR329 available from BioRad Laboratories, (Richmond, Calif.) and pPL and pKK223 available from Pharmacia, (Piscataway, N.J.

Expression vectors compatible with eucaryotic cells, preferably those compatible with vertebrate cells, can also be used. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/PML2d (International Biotechnologies, Inc.), and pTDT1 (ATCC, No. 31255).

In preferred embodiments, the eucaryotic cell expression vectors used include a selection marker that is effective in an eucaryotic cell, preferably a drug resistant selection marker. A preferred drug resistance marker is the gene whose expression results in neomycin resistance, i.e., the neomycin phosphotransferase (neo) gene. Southern et al., *J. Mol. Appl. Genet.*, 1:327–341 (1982).

The use of retroviral expression vectors to express the genes of the CR2 ligand-coding DNA segments is also contemplated. As used herein, the term "retroviral expression vector" refers to a DNA molecule that includes a promoter sequences derived from the long terminal repeat (LTR) region of a retrovirus genome.

In preferred embodiments, the expression vector is typically a retroviral expression vector that is preferably replication-incompetent in eucaryotic cells. The construction and use of retroviral vectors has been described by Sorge et al., *Mol. Cell. Biol.*, 4:1730–1737 (1984).

A variety of methods have been developed to operatively link DNA to vectors via complementary cohesive termini. For instance, complementary cohesive termini can be engineered into the CR2 ligand-coding DNA segments during a primer extension reaction by use of an appropriately designed polynucleotide synthesis primer, or by operatively linking a synthetic link containing one or more restriction sites. The vector, and DNA segment, if necessary, is cleaved with a restriction endonuclease to produce termini complementary to those of the DNA segment. The complementary cohesive termini of the vector and the DNA segment are then operatively linked (ligated) to produce a unitary double stranded DNA molecule.

The resulting construct is then introduced into an appropriate host to provide amplification and/or expression of the CR2 ligand-coding DNA segments, either separately or in combination. Cellular hosts into which a CR2 ligand-coding DNA segment-containing construct has been introduced are referred to herein as having been "transformed" or as "transformants", and such transformed cells, and cultures of said cells, are also contemplated by the present invention.

The host cell can be either procaryotic or eucaryotic. Bacterial cells are preferred procaryotic host cells and typically are a strain of E. coli such as, for example, the E. coli strain DH5 available from Bethesda Research Laboratories, Inc., Bethesda, Md. Preferred eucaryotic host cells include yeast and mammalian cells, preferably vertebrate cells such as those from a mouse, rat, monkey or human cell line.

Transformation of appropriate cell hosts with a recombinant DNA molecule of the present invention is accomplished by methods that typically depend on the type of vector used. With regard to transformation of procaryotic host cells, see, for example, Cohen et al., *Proceedings National Academy of Science*, USA, Vol. 69, P. 2110 (1972); and Maniatis et al., *Molecular Cloning, a Laboratory Manual*, Cold Spring Harbor Laboratory, Cold Spring Harbor, NY (1982). With regard to the transformation of vertebrate cells with retroviral vectors containing rDNAs, see for example, Sorge et al., *Mol. Cell. Biol.*, 4:1730–1737 (1984); Graham et al., *Virol.*, 52:456 (1973); and Wiglet et al., *Proceedings National Academy of Sciences*, USA, Vol. 76, P. 1373–1376 (1979).

Successfully transformed cells, i.e., cells containing a CR2 ligand-coding DNA segment operatively linked to a vector, can be identified by well known techniques. For example, cells from a population subjected to transformation with a subject rDNA can be cloned to produce monoclonal colonies. Cells form those colonies can be harvested, lysed and their DNA content examined for the presence of the rDNA using a method such as that described by Southern, *J. Mol. Biol.*, 98:503 (1975) or Berent et al., *Biotech.* 3:208 (1985).

In addition to directly assaying for the presence of a CR2 ligand-coding DNA segment, successful transformation can be confirmed by methods that detect the expressed CR2 ligand polypeptide. For example, samples of cells suspected of being transformed are assayed for the presence of the CR2 ligand by testing for CR2 ligand binding activity, or by using an antibody that immunoreacts with the CR2 ligand.

D. CR2 Ligands

The present invention contemplates a polypeptide, referred to as a CR2 ligand, capable of specifically binding to the CR2 receptor, as a functional ligand, and thereby effect (modulate) changes in CR2 receptor-containing cell status, such as to induce or inhibit proliferation, to inhibit EBV infection, and the like.

A subject CR2 ligand is further characterized by the presence of at least one of the following amino acid residue sequences:

—PAIVEAG—, or

—NSGVEA—.

In a preferred embodiment, a CR2 ligand includes the amino acid residue sequence —NSGVEA— or —PAIVEAG— and corresponds in sequence to a portion of the amino acid residue shown in FIGS. 1A-1I. In one version of this embodiment, a CR2 ligand has an amino acid residue sequence that corresponds, and preferably is identical, to the sequence shown in FIGS. 1A-1I from residue 1 to residue 700.

Preferred CR2 ligands have an amino acid residue sequence that corresponds, and preferably is identical, to a sequence shown in one of the formulae:

| NSGVEA | , |
| QNSGVEALI | , |
| TQNSGVEALI | , |
| VTQNSGVEALI | , |
| LVTQNSGVEALI | , |
| QNSGVEALIHAIL | , |
| QNSGVEALIHAI | , |
| QNSGVEALIH | , |
| PAIVEAG | , |
| KPAIVEAG | , |
| NKPAIVEAG | , |
| SNKPAIVEAG | , |
| PAIVEAGG | , |
| PAIVEAGGM | , and |
| PAIVEAGGMQ. | |

A subject polypeptide comprising a CR2 ligand includes any polypeptide, analog, or chemical derivative of a polypeptide whose amino acid residue sequence is shown herein so long as the polypeptide is capable of binding CR2 and modulating the function of a CR2-containing cell in a manner disclosed herein. Therefore, a present polypeptide can be subject to various changes, substitutions, insertions, and deletions where such changes provide for certain advantages in its use.

The term "analog" includes any polypeptide having an amino acid residue sequence substantially identical to a sequence specifically shown herein in which one or more residues have been conservatively substituted with a functionally similar residue and which displays the ability of a CR2 ligand as described herein. Examples of conservative substitutions include the substitution of one nonpolar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

Thus additional CR2 ligands contemplated by the present invention have an amino acid residue sequence that corresponds to one of the sequences represented by the formulae:

| QSNGVEALT | , |
| QNSGLEALT | , |
| QNSGLEALI | , |
| QSNGVEALI | , |
| QNSVGEALI | , |
| QPAIVEAG | , |
| QNAIVEAG | , |
| QPAIVEAL | , |
| QPAIVEALI | , |
| QPAIVEALT | , |
| QPAILEAG | , |
| QPAILEAGT | , |
| QPAIVEAGI | , |
| QNAIVEALI | , and |
| QNAIVEALT | . |

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

A subject polypeptide can be prepared using recombinant nucleic acid methodologies well known, some of which are disclosed herein above. For instance, DNA segments that encode a CR2 ligand are prepared and then ligated into an expression vector, and a host transformed therewith can be used to produce the polypeptide. The recombinant expression vectors so formed that are capable of expressing a subject polypeptide and methods of their use for producing a subject polypeptide are contemplated as part of the present invention.

A subject polypeptide can also be prepared using the solid-phase synthetic technique initially described by Merrifield, in J. Am. Chem. Soc. 85:2149-2154 (1963). Other polypeptide synthesis techniques may be found, for example, in M. Bodanszky et al., *Peptide Synthesis*, John Wiley & Sons, 2d Ed., (1976) as well as in other reference works known to those skilled in the art. A summary of polypeptide synthesis techniques may be found in J. Stuart and J. D. Young, *Solid Phase Peptide Synthesis*, Pierce Chemical Company, Rockford, Ill., 3d Ed., Neurath, H. et al., Eds., p. 104-237, Academic Press, New York, N.Y. (1976). Appropriate protective groups for use in such syntheses will be found in the above texts as well as in J. F. W. McOmie, *Protective Groups in Organic Chemistry*, Plenum Press, New York, N.Y. (1973).

In general, those synthetic methods comprise the sequential addition of one or more amino acid residues or suitably protected amino acid residues to a growing polypeptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amid linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence any remaining terminal and side group protecting groups (and solid support) are removed sequentially or concurrently, to provide the final polypeptide.

In another embodiment, a CR2 ligand is characterized by the presence of a plurality of polypeptide segments, each polypeptide segment being defined by the presence of one of the following amino acid residue sequences:

—PAIVEAG—, or

—NSGVEA—.

The included polypeptide segments can be adjacent and/or contiguous within the polypeptide chain, with adjacent segments being separated in the amino acid residue sequence of the polypeptide by one or more spacing residue. Preferably, the spacing residues make up a spacing segment in the range of about 1 to about 20, preferably about 5 to about 15, and more usually about 10, amino acid residues in length.

In addition, a subject polypeptide can contain a leader segment of 1 conveniently up to about 20, such as about 5, about 10 or about 15, amino acid residues located amino-terminal to the amino-terminal CR2 ligand-derived or spacing segment.

In a similar manner, a subject polypeptide need not end with the carboxy-terminal residue of a CR2 ligand-derived segment or spacer segment. A carboxy terminal tail segment can be present containing 1 conveniently up to about 20, such about 5, about 10 or about 15, amino acid residues.

Preferred polypeptides of the present invention having a plurality of segments are defined by the formula:

B—$(X_n$—NSGVEA—$Z_m)_a$—J,

In the above formula, B is an amino-terminal NH$_2$ group or a previously discussed leader segment; J is a carboxy-terminal COOH group or a previously discussed tail segment; X and Z are first and second, respectively, spacing segments whose amino acid residue sequences can be the same or different; n is either 1 or 0 such that when n is 1, X is present, and when n is 0, X is not present; m is either 1 or 0 such that when m is 1, Z is present, and when m is 0, Z is not present; and a is an integer from 2 to about 10, more preferably 2 to about 5 and usually 2 to 3, indicating the number of times the amino acid residue sequence in parenthesis is present (repeated) in the polypeptide primary structure. Preferably, the sequence in parenthesis corresponds in its entirety, and preferably is identical to, a portion of the amino acid residue sequence of CR2 ligand shown in FIG. 1. Preferred polypeptides are those whose formulas are shown in Table 1.

In another embodiment, a CR2 ligand is contemplated in which the included CR2 ligand polypeptides described above are present as a conjugate comprised of a plurality of said polypeptides operatively linked, by other than a peptide bond between the alpha-amino group and carboxy group of contiguous amino acid residues, where at least two of the linked polypeptides have an amino acid residue sequence corresponding to that represented by the formula:

B—$(X_n$—NSGVEA—$Z_m)_a$—J, wherein B, X, Z, J, n, m and a are defined as previously discussed except that a can also be the integer 1.

In preferred embodiments, a conjugate of this invention has a molecular weight of less than about 40,000 daltons, preferably less than about 20,000 daltons, and more preferably less than about 10,000 daltons. Typically, a subject conjugate has a molecular weight of no more than about 15,000 daltons, preferably no more than about 8,000 daltons, and usually no more than about 4,000 daltons. Preferably, the conjugate is dimeric or trimeric, i.e., consists essentially of two or three polypeptide chains, respectively.

A polypeptide conjugate of this invention is further characterized by its ability to bind CR2 receptor and thereby modulate CR2 containing cells as disclosed herein. The subject conjugates are also substantially free of toxicity toward lymphocytes at concentrations of about 20 micrograms per milliliter (ug/ml).

The techniques of polypeptide conjugation or coupling through activated functional groups presently known in the art are particularly applicable. See, for example, Aurameas, et al., *Scand. J. Immuno.*, Vol. 8, Suppl. 7:7–23 (1978) and U.S. Pat. No. 4,493,795, U.S. Pat. No. 3,791,932 and U.S. Pat. No. 3,839,153. In addition, a site directed coupling reaction can be carried out so that any loss of activity due to polypeptide orientation after coupling can be minimized. See, for example, Rodwell, et al., *Biotech.*, 3:889–894 (1985), and U.S. Pat. No. 4,671,958.

One or more additional amino acid residues may be added to the amino- or carboxy- termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

E. Therapeutic Compositions and Methods

Therapeutic compositions of the present invention contain a physiologically tolerable carrier together with a CR2 ligand, or CR2 polypeptide conjugate, as described above, dissolved or dispersed therein as an active ingredient. In a preferred embodiment, the therapeutic composition is not immunogenic when administered to a mammal or human patient.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose and other solutes.

Liquid compositions can also contain liquid phases in addition to and to the exclusion of water. Exemplary of such additional liquid phases are glycerin, vegetable oils such as cottonseed oil, and water-oil emulsions.

1. Methods of Modulating the Function of CR2-Containing Cells

Methods for modulating the function of CR2-containing cells in vivo or in vitro are contemplated by the present invention.

It has been discovered that CR2 ligands have the capacity to induce (modulate) changes in the present status of a CR2-containing cell, such as normal or neoplastic B lymphocytes. In addition, the CR2 ligands exhibit the modulating capacity on B lymphocytes from mammals such as mice, sheep, cattle, horses, and man. These changes include stimulation or inhibition of proliferation of the lymphocyte. The capacity of a CR2 ligand to inhibit, as compared to the capacity to stimulate, B lymphocytes depends on the structure of the ligand, and particularly on the number of CR2 ligand binding sites, and their relative spacing in the CR2 ligand.

The inhibitory or stimulator capacity of a CR2 ligand of the present invention can be readily determined by a variety of methods, such as by monitoring changes in the amount of thymidine uptake by cultured B lymphocytes in the presence of various amounts of CR2 ligand, as disclosed in Example 3.

A CR2 ligand is inhibitory if it contains only one CR2 ligand binding site. A CR2 ligand binding site is an amino acid residue sequence that corresponds, and is preferably identical, to a sequence represented by the formula —PAIVEAG— or —NSGVEA—.

Representative inhibitory CR2 ligands are the polypeptides:

NSGVEA,
QNSGVEALT,
QNSGVEALI, and
PAIVEAG.

Thus, in one embodiment the present invention provides for a method of inhibiting CR2 function on CR2-containing cells and comprises administering to a mammal a therapeutically effective amount of a physiologically tolerable composition containing an inhibitory CR2 ligand, thereby forming a CR2-ligand complex by the specific binding between the CR2 receptor and the CR2 ligand. The inhibitory CR2 ligand is administered to the mammal in a predetermined amount calculated to achieve the desired effect, i.e., in a therapeutically effective amount.

For instance, when used as an agent for inhibiting B lymphocyte proliferation, such as in a human patient displaying the symptoms of an autoimmune disease or in a patient with B cell lymphoma, the inhibitory CR2 ligand is administered in an amount sufficient to achieve a plasma concentration of at least about 0.8 ug/ml, preferably at least about 0.10 ug/ml, more preferably at least about 2 ug/ml, and usually 3 or 4 ug/ml.

In another embodiment, the present invention provides for a method of stimulating proliferation of a CR2-containing cell, particularly a B lymphocyte in, for example, a human exhibiting B cell immunodeficiencies, a B cell hybridoma cell line in culture to boost production of antibody molecules, and the like.

Thus, the present invention contemplates a method of stimulating CR2-containing cells in a mammal that comprises administering a therapeutically effective amount of a physiologically tolerable composition containing a stimulatory CR2 ligand to a mammal in a predetermined amount calculated to achieve the desired effect.

When used as an agent to stimulate B lymphocyte proliferation, such as a human displaying B cell immunodeficiencies, the stimulatory CR2 ligand is administered in an amount sufficient to achieve a plasma concentration of at least about 0.8 ug/ml, preferably at least about 0.1 ug/ml, more preferably at least about 2 ug/ml and usually 3 or 4 ug/ml.

A representative stimulatory CR2 ligand is a polypeptide having an amino acid residue sequence that corresponds to the sequence shown in FIGS. 1A-1I from residue 1 to residue 700.

The present invention also contemplates a method of stimulating B cell hybridoma cells in culture. A culture of B cell hybridoma cells is admixed with an effective amount of a stimulatory CR2 ligand and maintained under culture conditions for a time period sufficient to allow the admixed ligand to specifically bind any CR2 receptor present in the culture. An effective amount is that amount which produces a concentration of ligand in the culture sufficient to bind essentially all of the CR2 receptor present, and usually is at a concentration of about 100 ug to about 1 mg per ml.

It has also been discovered that antibodies directed against a CR2 ligand binding site have the capacity to inhibit CR2 function by competing for CR2 ligand. Therefore, anti-CR2 ligand antibody molecules that immunoreact with either of the CR2 ligand binding site polypeptides PAIVEAG or NSGVEA, and compositions containing those molecules, can be similarly used in a method for inhibiting CR2 function, including the inhibition of B lymphocyte proliferation.

Thus, in this related embodiment for inhibiting CR2 function, the physiologically tolerable composition administered contains a therapeutically effective amount of anti-CR2 ligand antibody molecules of this invention in an amount sufficient to immunoreact with the CR2 ligand present in the patient, thereby competing with native CR2 ligand for binding to CR2 and inhibiting normal CR2 ligand-induced CR2 functions.

The therapeutic compositions containing CR2 ligand or anti-CR2 ligand antibody molecules are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition of lymphoproliferation or androgen production desired. Precise amounts of active ingredient required to be administered depend on the judgment of the practitioner and are peculiar to each individual. However, suitable dosage ranges for systemic application are of the order of 0.01 to 10, preferably one to several, milligrams of active ingredient per kilogram bodyweight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nano molar to ten micromolar in the blood are contemplated.

2. Methods of Inhibition and Treatment of Epstein-Barr Virus Infection

Epstein-Barr virus infection of mammalian cells in an aqueous suspension, such as blood, is inhibited by methods of the present invention.

An aqueous suspension containing mammalian cells, such as B lymphocytes, is admixed with a therapeutically effective amount of a physiologically tolerable composition of CR2 ligand of the present invention and maintained for a time period sufficient to allow the CR2 ligand polypeptides of the composition to specifically bind any CR2 receptor present in the suspension. When the admixture contains a concentration of Epstein-Barr virus that is sufficient to infect the mammalian cells under normal physiological conditions when no pharmacological intervention or treatment is undertaken, the therapeutically effective amount of the CR2 ligand-containing composition utilized in this method is that which produces a concentration of CR2 ligand in the aqueous suspension sufficient to bind essentially all of the CR2 receptor present, and usually is at a concentration of about 100 ug to about 1 mg per ml.

When the method of treatment of the present invention is utilized to inhibit EBV infection in vivo the therapeutically effective amount of the therapeutic composition administered is that which produces a blood concentration of CR2 ligand sufficient to specifically bind the CR2 receptor present and available for EBV infection. Such a blood concentration is usually about 100 ug to about 1 mg of CR2 ligand per ml. It is contemplated that multiple administrations of the therapeutic composition of this invention over an appropriate time period and at a dosage level determined by a medical practitioner for the patient will be undertaken for the inhibition of EBV infection in a human patient. Typically, a CR2 ligand is administered substantially concurrently with either recurrence of infection in a chronically infected patient or upon initial exposure to EBV, such as on receipt of tissue from an EBV-seropositive donor. Alternatively, a CR2 ligand can be administered therapeutically to cure or ameliorate diseases in which EBV infection plays a role, such as mononucleosis, Burkitt's lymphoma and nasopharyngeal carcinoma.

As used herein, the terms "specifically bind", and "specifically attach", and grammatical forms thereof are used interchangeably and refer to non-random ligand binding, such as that which occurs between CR2 ligand and CR2.

In the method of treatment of the present invention, a pharmacological composition, as described above, is administered to a patient in any manner that will efficaciously inhibit the infection of mammalian cells, such as B lymphocytes, by EBV. Preferably, the composition is administered by either intravenous injection of a unit dosage or continuous intravenous infusion of a predetermined concentration of CR2 ligand of the present invention to a patient.

F. Antibody Compositions

An antibody of the present invention is a composition containing antibody molecules that immunoreact with a CR2 ligand of the present invention. A preferred antibody contains antibody molecules that immunoreact with a polypeptide having an amino acid residue sequence that corresponds to the sequence shown in FIGS. 1A–1I from residue 1 to residue 700, from residue 303 to residue 309, from residue 389 to residue 394, or from residue 388 to residue 396.

An antibody of the present invention is typically produced by immunizing a mammal with an inoculum containing a CR2 ligand and thereby induce in the mammal antibody molecules having immunospecificity for CR2 ligand. The antibody molecules are then collected from the mammal and isolated to the extent desired by well known techniques such as, for example, by using DEAE Sephadex to obtain the IgG fraction.

To enhance the specificity of the antibody, the antibodies may be purified by immunoaffinity chromatography using solid phase-affixed CR2 ligand. The antibody is contacted with solid phase-affixed CR2 ligand for a period of time sufficient for the CR2 ligand to immuno react with the antibody molecules to form a solid phase-affixed immunocomplex. The bound antibodies are separated from the complex by standard techniques.

The antibody so produced can be used in, inter alia, the diagnostic methods and systems of the present invention to detect CR2 ligand present in a body sample.

The word "inoculum" in its various grammatical forms is used herein to describe a composition containing a CR2 ligand of this invention as an active ingredient used for the preparation of antibodies against CR2 ligands. When a polypeptide is used to induce antibodies it is to be understood that the polypeptide can be used alone, or linked to a carrier as a conjugate, or as a polypeptide polymer, but for ease of expression the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies as already noted.

As already noted, one or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein, et al., *J. Infect. Dis.*, 147, 318–326 (1983) and the like, or the use of carbodiimide technology as in the use of a water-soluble carbodiimide to form amide links to the carrier. For a review of protein conjugation or coupling through activated functional groups, see Aurameas, et al., *Scand. J. ImmunL,* Vol. 8, Supp-1. 7, 7–23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose depends, among other things, on the species of animal inoculated, the body weight of the animal and the chosen inoculation regimen as is well known in the art. Inocula typically contain polypeptide concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

A monoclonal antibody is also contemplated by the present invention and is composed of monoclonal antibody molecules that immunoreact with a CR2 ligand of the present invention. Preferably, the monoclonal antibody molecules immunoreact with a polypeptide having an amino acid residue sequence that corresponds to the sequence shown in FIGS. 1A–1I from residue 303 to residue 309, from residue 389 to residue 394, from residue 388 to residue 396, or from residue 1 to residue 700.

A monoclonal antibody is typically composed of antibodies produced by clones of a single cell called a hybridoma that secretes (produces but one kind of antibody molecule. The hybridoma cell is formed by fusing an antibody-producing cell and a myeloma or other self-perpetuating cell line. The preparation of such antibodies were first described by Kohler and Milstein, Nature 256:495–497 (1975), which description is incorporated by reference. Other methods of producing monoclonal antibodies are also well known. The hybridoma supernates can be screened for immunoreactivity for a CR2 ligand or for inhibition of binding of CR2 ligand to CR2.

The monoclonal antibodies of this invention can be used in the same manner as disclosed herein for antibodies of the present invention.

G. Diagnostic Systems and Methods

1. Diagnostic systems

A diagnostic system in kit form of the present invention includes, in an amount sufficient for at least one assay, a CR2 ligand antibody or monoclonal antibody of the present invention, as a separately packaged reagent. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for the presence of or to quantitate anti-CR2 ligand antibodies in a sample, such as blood, plasma or serum, comprises a package containing at least one CR2 ligand of this invention. In another embodiment, a diagnostic system of the present invention for assaying for the presence or amount of CR2 ligand in a sample comprises a package containing an anti-CR2 ligand antibody composition of this invention.

In preferred embodiments, a diagnostic system of the present invention further includes a label or indicating means capable of signaling the formation of an immunocomplex comprised of either a CR2 ligand of this invention specifically bound to anti-CR2 ligand antibody molecules or an anti-CR2 ligand antibody molecule of this invention specifically bound to a CR2 ligand.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an antibody molecule that is part of an antibody or monoclonal antibody used in the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The label can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189-231 (1982), which is incorporated herein by reference.

In preferred embodiments, the label is an enzyme, such as horseradish peroxidase (HRP), glucose oxidase, alkaline phosphatase or the like. In such cases where the principal label is an enzyme such as HRP or glucose oxidase, additional reagents are required to visualize the fact that a antibody-antigen complex (immunoreactant) has formed. Such additional reagents for HRP include hydrogen peroxide and an oxidation dye precursor such as diaminobenzidine. An additional reagent useful with HRP is 2,2'-azino-di-(3-ethyl-benzthiazoline-6-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such $^{111}$indium of $^3H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3-46 (1981). The techniques of protein conjugation or coupling through activated functional groups are particularly applicable. See, for example, Auramas, et al., *Scand. J. Immunol*, vol. 8 suppl. 7:7-23 (1978), Rodwell et al., Biotech., 3:889-894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself a protein expression product, polypeptide, or polypeptide conjugate or aggregate of the present invention. Exemplary specific binding agents are antibody molecules, complement proteins or fragments thereof, protein A, and the like. For detecting CR2 ligand, the specific binding agent can bind the anti-CR2 ligand antibody molecules of this invention when it is present as part of an immunocomplex. When detecting patient anti-CR2 antibodies, anti-human Fc antibodies are conveniently used. In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the presence or quantity of CR2 ligand or anti-CR2 ligand antibodies in a body fluid sample such as blood serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites, et al, published by Lange Medical Publications of Los Altos, Calif. in 1982, and in U.S. Pat. No. 3,654,090; U.S. Pat. No. 3,850,752; and U.S. Pat. No. 4,016,043, which are all incorporated herein by reference. Thus, in preferred embodiments, the CR2 ligand or an anti-CR2 ligand antibody molecule of the present invention can be affixed to a solid matrix to form a solid support that is separately packaged in the subject diagnostic systems.

The reagent is typically affixed to the solid matrix by adsorption from an aqueous medium although other modes of affixation, well known to those skilled in the art can be used.

Useful solid matrices are well known in the art. Such materials include the cross-linked dextran available under the trademark SEPHADEX from Pharmacia Fine Chemicals (Piscataway, NJ); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microliter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. The term "package" refers to a solid matrix or material such as glass, plastic, paper, foil and the like capable of holding within fixed limits a diagnostic reagent such as a polypeptide, antibody or monoclonal antibody of the present invention. Thus, for example, a package can be a glass vial used to contain a contemplated diagnostic reagent or it can be a microtiter plate well to which microgram quantities of a contemplated diagnostic reagent have been operatively affixed, i.e., linked so as to be capable of being immunologically bound by an antibody or CR2 ligand to be detected.

2. Diagnostic Methods

The present invention also contemplates any diagnostic method that results in detecting CR2 ligand or anti-CR2 ligand antibodies in a body fluid sample using CR2 ligand or antibody molecule-containing compositions of this invention. Thus, while exemplary methods are described herein, the invention is not so limited.

To detect the presence of either anti-CR2 ligand antibodies or CR2 ligand in a patient, a bodily fluid sample such as blood, plasma or serum from the patient is contacted by admixture under biological assay conditions with a CR2 ligand or anti-CR2 ligand antibody molecule of the present invention, respectively, to form an immunoreaction admixture. The admixture is then maintained for a period of time sufficient to allow the formation of a CR2 ligand-antibody molecule immunoreaction product (immunocomplex). The presence of the complex is indicative of anti-CR2 ligand antibodies or of CR2 ligand, respectively. The complex can then be detected as described herein. In preferred embodiments the diagnostic methods of the present invention are practiced in a manner whereby the immunocomplex is formed and detected in a solid phase, as disclosed for the diagnostic systems herein.

Biological assay conditions are those that maintain the biological activity of the CR2 ligand molecules and the anti-CR2 antibodies in the immunoreaction admixture. Those conditions include a temperature range of about 4 C. to about 45 C., preferably about 37 C., a pH value range of about 5 to about 9, preferably about 7, and an ionic strength varying from that of distilled water to that of about one molar sodium chloride, preferably about that of physiological saline. Methods for optimizing such conditions are well known in the art.

Also contemplated are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel proteins, methods and systems. Exemplary detection means include methods known as biosensors and include biosensing methods based on detecting changes in the reflectivity of a surface changes in the absorption of an evanescent wave by optical fibers or changes in the propagation of surface acoustical waves.

EXAMPLES

The following examples are given for illustrative purposes only and do not in any way limit the scope of the invention.

1. Cloning A cDNA That Encodes A CR2 Ligand

A lambda gt10 cDNA library obtained from a human B lymphoblastoid cell line Raji (ATCC #CCL 86) known to produce alpha-BCGF (B cell growth factor) activity [Corbel et al., Immunol. Rev., 78:51 (1983)] was obtained from Clontech (Palo Alto, Calif.). Oligonucleotides encoding the LYNVEA motif on C3 fragments were used to screen the cDNA library and a clone, lambda 9-4, was ultimately isolated that contained an EcoR I insert of 3.1 kilobase pairs (kb). The insert was sequenced and found to contain an open reading frame that encodes a 700 amino acid residue protein. The nucleotide sequence and encoded amino acid sequence for the lambda 9-4 insert are shown in FIGS. 1A-1K. A comparison of the lambda 9-4 insert sequence with sequence data banks showed no significant homology to any known protein or gene. Due to its uniqueness, the CR2 ligand-encoding insert in the lambda 9-4 cDNA is designated a DNA segment that encodes a new CR2 ligand protein.

2. Synthetic Polypeptides

Synthetic polypeptides having an amino acid residue sequence that corresponds to portions of the CR2 ligand sequence shown in FIG. 1, from residue 303 to residue 309 (PAIVEAG), and from residue 389 to residue 394 (NSGVEA), and those polypeptides shown in Tables 1 and 2, were obtained from Multiple Peptide Systems (La Jolla, Calif.) after their synthesis by the classical solid-phase technique described by Merrifield, Adv. Enzymol., 32:221-96 (1969).

3. Inhibition of Cell Proliferation Using CR2 Ligands

A B cell proliferation assay system was used to examine the ability of various CR2 ligand polypeptides to inhibit B lymphocyte proliferation.

Cultures of the cell lines shown in Table 1 were established at a density of $2 \times 10^4$ cells per well of a 96 well microtiter plate in serum-free ISCOVE'S medium. To the cultures were added varying amounts of the polypeptides indicated in Table 1 at various concentrations from zero to 500 ug per ml of culture, and the cell-polypeptide admixtures were then maintained for 24 hours to 48 hours at 37 C. Thereafter, 1 uCi of $^3$H-thymidine label was admixed with each culture and maintained for 4 hours at 37 C. to allow the label to incorporate into proliferating cells in the cultures. After 4 hours the cultures were harvested and the incorporated label was measured by standard techniques.

The results of the above assay procedure are shown in Table 1.

TABLE 1

CR2 Ligand Polypeptides Inhibit B Cell Proliferation

| Polypeptides[c] tested | Human Inhibition[b] of: | | | Murine Inhibition[b] of: | | | |
|---|---|---|---|---|---|---|---|
| | EBV-induced peripheral B cell proliferation | B cell lymphoma Raji | T cell lymphoma HSB2 | LPS-induced splenic B cell proliferation | B cell lymphoma A20 | B cell lymphoma 38C13 | T cell lymphoma BW5147 |
| C3 QLYNVEATS | + | ++ | − | ++ | + | + | − |
| 9-4 QNSGVEALI | +++ | +++ | − | +++ | +++ | +++ | − |
| NSGVEA | N.T.[d] | +++ | − | N.T. | N.T. | N.T. | N.T. |
| QNSGVEALT | N.T. | +++ | − | N.T. | N.T. | N.T. | N.T. |
| control peptides: | | | | | | | |
| SPGRGD | − | − | − | − | − | − | − |
| GRGDSP | − | − | − | − | − | − | − |

[a] Each cell line was cultured as described in Example 3 with the following exceptions: human peripheral B cells were cultured with EBV (strain B95/8) at a multiplicity of infection in excess of 1.0 EBV units per cell and was admixed simultaneously with admixture of polypeptide; mouse splenic B cells were cultured with the admixed polypeptides in combination with lipopolysaccharide (LPS) a 25 ug per ml.
[b] Inhibition is expressed as the amount of added polypeptide required to exhibit half-maximal inhibition. −: no inhibition at 500 ug polypeptide per, ml; +: half-maximal inhibition at 200–500 ug/ml; ++: at 50–200 ug/ml; +++: at 5–50 ug/ml.
[c] Polypeptides were prepared as described in Example 2.
[d] N.T. indicates not tested.

The results in Table 1 show that a polypeptide having the CR2 ligand sequence QNSGVEALI strongly inhibits B cell proliferation in all assays used. The polypeptide did not inhibit the CR2 receptor-negative T cell lines, HSB2 or BW5147, indicating that the CR2 ligand polypeptide is specific for CR2-containing cells and does not inhibit proliferation due to toxicity of the polypeptide. RGD-containing control polypeptides derived from fibronectin also did not exhibit inhibiting effects. Because EBV-induced proliferation of B cells is a CR2-mediated event (Cooper et al., Ann. Rev. Immunol., 6:85, 1988), the results further indicate that the CR2 ligand specifically binds CR2.

The CR2 ligand polypeptides NSGVEA and QNSGVEALT also strongly inhibit B cell proliferation, as measured by the Raji cell assay. Thus, by this proliferation inhibition assay, inhibitory CR2 ligand polypeptides are identified.

4. Inhibition of Direct Binding of CR2 Ligands to CR2

Fresh blood from a healthy donor was collected and maintained at room temperature for 2 hours. Then the blood was centrifuged at 2000 x g for about 10 min and the resulting supernatant was collected. Five mg of Zymosan A particles (Sigma Chemical Co., St. Louis, Mo.) were boiled for 30 min in 20 ml of 150 mM NaCl and washed three times in phosphate-buffered saline (PBS) to form activated Zymosan. One mg of activated Zymosan particles was admixed with 0.5 ml of blood supernatant and maintained at 37 C. for 30 min, and then was washed 3 times in PBS. The washed particles were then resuspended in PBS at a concentration of 0.5 mg/ml to form a $C_3$-coated Zymosan composition.

Cultures containing $10^5$ Raji or HSB2 cells were admixed with varying amounts (zero to 200 ug) of the polypeptides shown in Table 2 in a volume of 100 microliters (ul) of culture medium and the admixture was maintained at 37C for 30 min to allow CR2 ligand polypeptides to bind any CR2 receptor present on the cells. Thereafter, 50 ul of $C_3$-coated Zymosan composition was added to each culture, the cultures were subjected to centrifugation for 1 min at 600×g and then maintained at 37 C. for 30 min. The maintained cultures were then washed with prewarmed culture medium to rinse off non-bound particles. Washed cultures were observed using a microscope to detect and count the number of particles (rosettes) attached per cell. More than 3 rosettes per cell was counted as $C_3$ specific binding. Inhibition is expressed as the percent decrease in bound rosettes when comparing binding in the presence or absence of admixed polypeptide. The results are shown in Table 2.

TABLE 2

Inhibition of Direct Binding of $C_3$-Coated Zymosan to Cells Using CR2 Ligand

| Peptide | Sequence | Inhibition |
|---|---|---|
| C3 | LYNVEAT | 70% |
| 9-4 | NSGVEA | 35% |
| control | SRRGDMS | 0% |
| no peptide | — | 0% |

The results in Table 2 show that the CR2 ligand polypeptide NSGVEA significantly inhibits direct binding of complement $C_3$ fragments to CR2 receptor on Raji cells. As a positive control, a complement $C_3$ polypeptide having the $C_3$ binding site motif shows, as expected, strong inhibition of binding between $C_3$ and CR2 receptor.

5. Preparation Of CR2 Ligand Using An Expression Vector a. Prokaryotic Vector Preparation The lambda 9-4 insert produced in Example 1, was subcloned into the EcoR I restriction site of the expression vector, plasmid Bluescript 2 SK+(Stratagene, La Jolla, Calif.), to produce the plasmid, p9-4. Plasmid p9-4 was then digested with the restriction enzymes Avr II and Xba I to excise a 3' flanking untranslated portion of the insert, and was religated by union of the remaining cohesive termini generated by Avr II and Xba I, which are isoschitzomers. The religated plasmid was digested with Xho I to form a linearized plasmid, and was then treated with mung bean nuclease to blunt end the previously cohesive Xho I termini. The blunt-ended plasmid was then religated to form a circular plasmid, designated pBS 9-4. The plasmid pBS 9-4 as presently constructed can express a fusion protein that consists of about 30 amino acid residues at the amino terminus of the fusion protein, that are derived from the betagalactosidase gene present in the original plasmid Bluescript 2 SK+, and about 700 amino acids at the carboxy terminus of the fusion protein, that are derived from the lambda insert encoding the CR2 ligand protein.

b. Prokaryotic Vector Expression of CR2 Ligand

Plasmid pBS 9-4, prepared in Example 5a, is introduced into the E. coli strain XLI-Blue (Stratagene) by transformation, and a culture of transformed bacteria is then cultured in the presence of IPTG to induce expression of fusion protein off of the beta-galactosidase promoter present on the expression vector. Whole cell extracts from both induced and control (uninduced) cell cultures of the bacteria containing pBS 9-4 are then prepared and the extracts analyzed by polyacrylamide gel electrophoresis in the presence of SDS (PAGE-SDS) according to the procedure of Laemmli (Nature, 227:680, 1971). The resulting PAGE-SDS gels, when strained with Coomassie blue, exhibit a band having a molecular weight of about 80,000 daltons that is present in higher amounts in the induced extracts relative to the uninduced extracts. The 80,000 dalton band is the expected size for a fusion protein comprised of 30 amino acid residues from betagalactosidase fused to 700 residues from the CR2 ligand-encoding gene. The 80,000 dalton band is not present in induced extracts prepared using cells transformed with the control, plasmid Bluescript.

c. Eukaryotic Vector Preparation pCMV 9-4: The religated plasmid produced after isoschitzomer ligation in Example 5a is digested with XbaI to form a linearized plasmid with cohesive XbaI termini. The cohesive termini are filled in by treating the linearized plasmid with the klenow fragment of E. coli DNA polymerase and then XhoI linkers are blunt end ligated onto the filled in termini of the linearized plasmid. The linker-modified plasmid is then digested with XhoI to produce cohesive termini and to excise an XhoI DNA segment of about 2.1 kb that includes the CR2 ligand-encoding gene.

The 2.1 kb DNA segment is isolated from the other nucleic acid products of the Xho I digestion by agarose gel electrophoresis, and the isolated segment is ligated into the Xho I site of the eukaryotic expression vector pCMVneo (Karasuyama et al., Eur. J. Immunol., 18:97, 1988) to form a mixture of plasmids in which the insert is present within pCMVneo in several possible orientations. The formed mixture of plasmids are collectively transformed into E. coli, individually isolated, and individually characterized by restriction enzyme digestion with BamH I and Hinc II and electrophoresis on 1% agarose. The isolated plasmid that exhibits a restriction pattern that includes a DNA segment of 1.6 kb and not 1.36 kb is selected as having the proper orientation for expression of the CR2 ligand encoding gene, and is designated pCMV 9-4.

pMSG 9-4: Plasmid pBS 9-4, prepared in Example 5a, is digested with Not I to form a linearized plasmid with cohesive Not I termini. The cohesive termini are filled in by treating the linearized plasmid with the klenow fragment of E. coli DNA polymerase and then XhoI linkers are blunt end ligated onto the filled in termini of the linearized plasmid. The linker-modified plasmid is then digested with XhoI to produce cohesive XhoI termini and further digested with SalI to excise a DNA segment of about 2.1 kb having one XhoI and one SalI termini that includes the CR2 ligand-encoding gene.

The 2.1 kb DNA segment is isolated from the other nucleic acid products of the XhoI and SalI digestion by agarose gel electrophoresis, and the isolated segment is ligated into the eukaryotic expression vector pMSG (Pharmacia LKB Biotechnology, Piscataway, N.J.) at the XhoI and SalI sites contained therein to form plasmid pMSG 9-4.

d. Eukaryotic Vector Expression of CR2 ligand

Plasmid pCMV 9-4, prepared in Example 5c, is introduced into murine L cells (ATCC # CCL 1) by transfection using the calcium phosphate technique and selection in the presence of the drug G418 to produce a transformed cell culture comprising L cells that contain the expression vector pCMV 9-4, designated as L/pCMV 9-4.

Culture supernatant is collected from a culture of L/pCMV 9-4 cells, and is analyzed on PAGE-SDS as described in Example 5b. Electrophoresed proteins contained in the resulting PAGE-SDS gel are electrophoretically transferred from the gel to a nitrocellulose sheet according to the Western blot technique of Towbin et al., (Proc. Natl. Acad. Sci. USA, 75:4350–54, 1979), and the resulting blot (solid-phase affixed antigen) is then immunoreacted with an antibody composition containing anti-CR2 ligand antibody molecules prepared as in Example 6, to form an immunoblot containing an immunoreaction product affixed thereto. The immunoreaction product is detected using a picoBlue Immunoscreening Kit (Stratagene) with anti-rabbit second antibody according to the manufacturer's instructions. The results of detecting immunoreaction product in the immunoblot show a band having a molecular weight of about 77,000 daltons present in supernatant samples obtained from L/pCMV 9-4 cultures, but not present in control samples of supernatant from cultures of L/pCMVneo. The 77,000 dalton band is the approximate size expected of an expressed CR2 ligand protein having 700 amino acid residues.

Plasmid pMSG 9-4, prepared in Example 5c, is introduced into L cells as described above for plasmid pCMV 9-4, except that selection is carried out as described by Mulligan et al. (Proc. Natl. Acid. Sci. USA, 78:2072, 1981) for transformants that contain the E. coli xanthine-guanine phosphoribosyltransferase gene (gpt). Transformed cultures are cultured as for L/pCMV 9-4 and culture supernatant is harvested to produce expressed CR2 ligand from the L/pMSG 9-4 transformed cell cultures. Upon analysis by Western blotting, an expressed CR2 ligand is detected as a band having a molecular weight of about 77,000 daltons.

6. Production of Anti-CR2 Ligand Antibodies

Polypeptide NSGVEALI, prepared as described in Example 2, was conjugated to bovine serum albumin (BSA) at an equal weight ratio using the glutaraldehyde coupling procedure of Aurameas et al. (Scand. I. Immunol., 1:7–23, 1978). New Zealand white rabbits were each injected with an immunogen containing 2.5 mls of a PBS suspension containing 1.25 mls complete Freund's adjuvant and o.5 mg of polypeptide in a polypeptide-BSA conjugate. Thereafter, each rabbit was boosted with the same immunogen, 7, 14, and 21 days after the first immunization, except that incomplete Freund's adjuvant was used. About 28 days after the first immunization, sera was collected from the immunized rabbits and used to detect anti-polypeptide immunoreactivity in a Western blot procedure as described in Example 5. The results indicate that the anti-polypeptide antisera contains antibodies that immunoreact with a protein on the blots of about 77,000 daltons, identified as an expressed CR2 ligand.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. A CR2 ligand consisting essentially of a polypeptide having an amino acid residue sequence selected from the group consisting of NSGVEA,
QNSGVEALI,
TQNSGVEALI,
VTQNSGVEALI,
LVTQNSGVEALI,
QNSGVEALIHAIL,
QNSGVEALIHAI,
QNSGVEALIH,
PAIVEAG,
KPAIVEAG,
NKPAIVEAG,
SNKPAIVEAG,
PAIVEAGG,
PAIVEAGGM, and
PAIVEAGGMQ, said ligand having the ability to specifically bind CR2 receptor.

2. A CR2 ligand consisting essentially of a polypeptide having an amino acid residue sequence selected form the group consisting of:

QSNGVEALT,
QNSGLEALT,
QNSGLEALI,
QSNGVEALI,
QNSVGEALI,
QPAIVEAG,
QNAIVEAG,
QPAIVEAL,
QPAIVEALI,
QPAIVEALT,
QPAILEAG,
QPAILEAGT,
QPAIVEAGI,
QNAIVEALI, and
QNAIVEALT, said ligand having the ability to specifically bind CR2 receptor.

* * * * *